US011679171B2

(12) United States Patent
Provost et al.

(10) Patent No.: US 11,679,171 B2
(45) Date of Patent: Jun. 20, 2023

(54) APPARATUS AND METHOD FOR DISINFECTING SUBSTANCES AS THEY PASS THROUGH A PIPE

(71) Applicant: Steribin, LLC, St. George, UT (US)

(72) Inventors: Wayne Provost, Ivins, UT (US); Jonathan M. Cole, St. George, UT (US); Jeffrey Mel Glauser, Santa Clara, UT (US)

(73) Assignee: Steribin, LLC, St. George, UT (US)

( * ) Notice: Subject to any disclaimer, the term of this patent is extended or adjusted under 35 U.S.C. 154(b) by 0 days.

(21) Appl. No.: 17/746,580

(22) Filed: May 17, 2022

(65) Prior Publication Data

US 2022/0387642 A1    Dec. 8, 2022

Related U.S. Application Data

(60) Provisional application No. 63/208,318, filed on Jun. 8, 2021.

(51) Int. Cl.
*A61L 2/10* (2006.01)
*A61L 2/26* (2006.01)
*A23L 3/28* (2006.01)
*C02F 1/32* (2023.01)

(52) U.S. Cl.
CPC ............ *A61L 2/10* (2013.01); *A61L 2/26* (2013.01); *A23L 3/28* (2013.01); *A23V 2002/00* (2013.01); *C02F 1/325* (2013.01); *C02F 2303/04* (2013.01)

(58) Field of Classification Search
None
See application file for complete search history.

(56) References Cited

U.S. PATENT DOCUMENTS

| | | | |
|---|---|---|---|
| 2,090,973 | A | 8/1937 | Basham |
| 2,254,977 | A | 9/1941 | Prang |
| 2,359,477 | A | 10/1944 | Hoern |
| 2,365,306 | A | 12/1944 | Swebilius |
| 2,400,389 | A | 5/1946 | Cavallilto |
| D214,353 | S | 6/1969 | Oxford et al. |

(Continued)

FOREIGN PATENT DOCUMENTS

| | | |
|---|---|---|
| AU | 764360 B2 | 8/2003 |
| AU | 768839 B2 | 1/2004 |

(Continued)

OTHER PUBLICATIONS

Tsa, Youtube Video (Year: 2016).

(Continued)

*Primary Examiner* — Andrew Smyth
(74) *Attorney, Agent, or Firm* — Gurr Brande & Spendlove, PLLC; Robert A. Gurr

(57) ABSTRACT

A disinfecting apparatus includes a pipe configured to allow disinfecting light to penetrate therein to disinfect powder, liquid, or other substances. In some examples, the pipe has a window with a disinfecting light coupled to the exterior of the pipe and positioned to shine disinfecting light through the window so as to expose the substances passing therethrough. Because the disinfecting light is external to the pipe, repair and replacement of the disinfecting light is quickly and easily performed. Additionally, the disinfecting light may be retrofitted to current pipes.

2 Claims, 8 Drawing Sheets

(56) References Cited

U.S. PATENT DOCUMENTS

| | | |
|---|---|---|
| 3,954,407 A | 5/1976 | Andary et al. |
| 3,955,922 A | 5/1976 | Moulthrop |
| 4,088,445 A | 5/1978 | Ellis |
| 4,100,415 A | 7/1978 | Blaisdell et al. |
| D264,089 S | 4/1982 | Reid et al. |
| 4,417,607 A | 11/1983 | Scholle et al. |
| 4,530,202 A | 7/1985 | Powell et al. |
| 4,625,119 A | 11/1986 | Murdock |
| 4,669,346 A | 6/1987 | Benedict |
| 4,681,203 A | 7/1987 | Kornylak |
| 4,694,180 A | 9/1987 | Salisbury et al. |
| 4,757,205 A | 7/1988 | Latel et al. |
| 4,772,795 A | 9/1988 | Sakurai et al. |
| 4,793,507 A | 12/1988 | Delplanque |
| 4,803,364 A | 2/1989 | Ritter |
| 4,806,770 A | 2/1989 | Hylton et al. |
| D301,611 S | 6/1989 | Peterson et al. |
| 4,877,964 A | 10/1989 | Tanaka et al. |
| 4,888,487 A | 12/1989 | Ritter |
| 4,906,851 A | 3/1990 | Beasley et al. |
| 4,934,644 A * | 6/1990 | Nagy .............. H02G 3/105 24/339 |
| 4,973,847 A | 11/1990 | Lackey et al. |
| 4,975,587 A | 12/1990 | Min-Jenn |
| 5,008,933 A | 4/1991 | Kao et al. |
| 5,019,256 A | 5/1991 | Ifill et al. |
| 5,023,460 A | 6/1991 | Foster et al. |
| 5,126,572 A | 6/1992 | Chu |
| 5,127,521 A | 7/1992 | Bourque |
| 5,160,699 A | 11/1992 | Siegal |
| 5,225,172 A | 7/1993 | Meyler et al. |
| D342,992 S | 1/1994 | Robertson |
| 5,288,647 A | 2/1994 | Zimlich et al. |
| D348,075 S | 6/1994 | Meyer |
| 5,396,557 A | 3/1995 | Tonci |
| 5,487,877 A | 1/1996 | Choi |
| D367,486 S | 2/1996 | Bunker et al. |
| 5,514,871 A | 5/1996 | Hayes et al. |
| 5,547,635 A | 8/1996 | Duthie, Jr. |
| 5,588,549 A | 12/1996 | Furtner |
| D413,341 S | 8/1999 | Gellerson et al. |
| 5,958,336 A | 9/1999 | Duarte |
| 5,979,472 A | 11/1999 | Lowery et al. |
| D418,528 S | 1/2000 | Honjo et al. |
| 6,030,099 A | 2/2000 | McDermott |
| 6,039,928 A | 3/2000 | Roberts |
| 6,132,784 A | 10/2000 | Brandt et al. |
| D434,613 S | 12/2000 | Tramontina |
| 6,192,948 B1 | 2/2001 | Claessens et al. |
| 6,278,122 B1 | 8/2001 | Gagnon |
| 6,301,359 B1 | 10/2001 | Roberts |
| 6,365,113 B1 | 4/2002 | Roberts |
| 6,458,331 B1 | 10/2002 | Roberts |
| 6,490,351 B1 | 12/2002 | Roberts |
| 6,592,816 B1 | 7/2003 | Ebel et al. |
| 6,702,985 B1 | 3/2004 | Taggart et al. |
| 6,720,950 B2 | 4/2004 | Cheng |
| 6,730,923 B1 | 5/2004 | May et al. |
| D502,546 S | 3/2005 | Shin |
| 6,877,248 B1 | 4/2005 | Cross et al. |
| 6,903,924 B1 | 6/2005 | Tyner |
| 6,974,223 B2 | 12/2005 | Krietzman |
| 7,068,361 B2 | 6/2006 | Cimino et al. |
| D542,929 S | 5/2007 | Shin |
| 7,273,300 B2 | 9/2007 | Mrakovich |
| 7,372,044 B2 | 5/2008 | Ross |
| D573,474 S | 7/2008 | Beam et al. |
| D584,417 S | 1/2009 | Massee |
| D593,262 S | 5/2009 | Gong |
| 7,692,159 B2 | 4/2010 | Lane et al. |
| D615,257 S | 5/2010 | Helm |
| D616,563 S | 5/2010 | Huck et al. |
| 7,825,325 B2 | 11/2010 | Kennedy et al. |
| 7,888,657 B1 | 2/2011 | Zadro |
| 8,084,752 B2 | 12/2011 | Ranta et al. |
| 8,177,383 B2 | 5/2012 | Reuben |
| 8,197,087 B2 | 6/2012 | Sobue et al. |
| 8,283,639 B2 | 10/2012 | Lane et al. |
| 8,431,910 B1 | 4/2013 | Perry |
| 8,662,705 B2 | 3/2014 | Roberts |
| 8,765,072 B2 | 7/2014 | Morneault |
| 9,125,957 B2 | 9/2015 | Freue et al. |
| 9,233,179 B2 | 1/2016 | Ranta et al. |
| 9,364,573 B2 | 6/2016 | Deshays et al. |
| 10,413,625 B2 | 9/2019 | Pangan et al. |
| 10,647,461 B2 | 5/2020 | Altmann et al. |
| 10,682,432 B2 | 6/2020 | Pangan et al. |
| 10,842,894 B1 | 11/2020 | Provost et al. |
| D920,487 S | 5/2021 | Provost et al. |
| 11,072,543 B2 * | 7/2021 | Benzerrouk ............ C02F 1/325 |
| 2003/0048256 A1 | 3/2003 | Salmon |
| 2003/0108130 A1 * | 6/2003 | Tucker ................. F16L 3/133 375/345 |
| 2003/0155531 A1 | 8/2003 | Clark et al. |
| 2004/0022668 A1 | 2/2004 | Kitchen |
| 2004/0028553 A1 | 2/2004 | Panico |
| 2004/0046795 A1 | 3/2004 | Josephson et al. |
| 2004/0118427 A1 | 6/2004 | Palfy et al. |
| 2004/0127355 A1 | 7/2004 | Manu |
| 2004/0197248 A1 | 10/2004 | Hasegawa et al. |
| 2004/0265193 A1 | 12/2004 | Panice et al. |
| 2005/0028744 A1 | 2/2005 | Gantt |
| 2005/0031485 A1 | 2/2005 | Wen |
| 2005/0052410 A1 | 3/2005 | Chen |
| 2005/0069465 A1 | 3/2005 | McEllen |
| 2005/0212239 A1 | 9/2005 | Carter |
| 2005/0269254 A1 | 12/2005 | Roitman |
| 2006/0186358 A1 | 8/2006 | Couvillion |
| 2006/0188389 A1 | 8/2006 | Levy |
| 2006/0217789 A1 | 9/2006 | Perez |
| 2007/0113421 A1 | 5/2007 | Uhara et al. |
| 2007/0222554 A1 | 9/2007 | Hart |
| 2007/0274879 A1 | 11/2007 | Millikin |
| 2008/0065264 A1 | 3/2008 | Omura et al. |
| 2008/0067418 A1 | 3/2008 | Ross |
| 2008/0085228 A1 | 4/2008 | Yamazaki et al. |
| 2008/0265179 A1 | 10/2008 | Havens et al. |
| 2009/0193607 A1 | 8/2009 | Adell et al. |
| 2009/0218512 A1 | 9/2009 | Ranta et al. |
| 2009/0252646 A1 | 10/2009 | Holden et al. |
| 2009/0317798 A1 | 12/2009 | Heid et al. |
| 2010/0044582 A1 | 2/2010 | Cooper et al. |
| 2010/0124520 A1 | 5/2010 | Calvert |
| 2010/0266445 A1 | 10/2010 | Campagna |
| 2011/0158862 A1 | 6/2011 | Kim et al. |
| 2011/0256019 A1 | 10/2011 | Gruen et al. |
| 2012/0019488 A1 | 1/2012 | Mccarthy |
| 2012/0160638 A1 | 6/2012 | Baker et al. |
| 2012/0182755 A1 | 7/2012 | Wildner |
| 2012/0211645 A1 | 8/2012 | Tullo et al. |
| 2012/0280147 A1 | 11/2012 | Douglas |
| 2013/0004367 A1 | 1/2013 | Roberts |
| 2013/0240756 A1 | 9/2013 | Segal |
| 2013/0277574 A1 | 10/2013 | Dayton |
| 2014/0322070 A1 | 10/2014 | Thomas |
| 2015/0028228 A1 | 1/2015 | Almasy et al. |
| 2015/0115172 A1 | 4/2015 | Freue et al. |
| 2015/0298906 A1 | 10/2015 | Marastoni |
| 2016/0101201 A1 | 4/2016 | Franc et al. |
| 2017/0028089 A1 | 2/2017 | Garrett |
| 2018/0343898 A1 | 12/2018 | Alzeer et al. |
| 2020/0247689 A1 * | 8/2020 | McNulty ................ C02F 1/722 |
| 2020/0392019 A1 * | 12/2020 | Benzerrouk ............ C02F 1/325 |
| 2021/0023248 A1 | 1/2021 | Townsend et al. |
| 2021/0077644 A1 | 3/2021 | Provost et al. |

FOREIGN PATENT DOCUMENTS

| | | |
|---|---|---|
| BE | 531883 | 12/1957 |
| CA | 2316086 C | 2/2002 |
| CA | 2365306 C | 1/2005 |
| CA | 2359477 C | 7/2005 |
| CN | 201184995 Y | 1/2009 |
| CN | 101393468 A | 3/2009 |

(56) References Cited

FOREIGN PATENT DOCUMENTS

| | | | |
|---|---|---|---|
| CN | 201223570 Y | | 4/2009 |
| CN | 208175932 U | * | 12/2018 |
| DE | 3221392 A1 | | 12/1983 |
| DE | 29720530 U1 | | 1/1998 |
| DE | 10332771 A1 | | 3/2005 |
| EP | 1051199 A1 | | 7/2009 |
| EP | 0493372 A2 | | 6/2010 |
| FR | 2631240 A2 | | 11/1989 |
| GB | 2363332 B | | 4/2003 |
| GB | 2363281 B | | 8/2003 |
| GB | 2383225 B | | 8/2003 |
| GB | 2387530 A | | 10/2003 |
| GB | 2421220 A | | 6/2006 |
| GB | 2422807 A | | 8/2006 |
| GB | 2424971 A | | 10/2006 |
| GB | 2446387 A | | 8/2008 |
| JP | 61012769 A | | 1/1986 |
| JP | 4061694 A | | 2/1992 |
| JP | 4364644 A | | 12/1992 |
| JP | 6154300 A | | 6/1994 |
| JP | 7160362 A | | 6/1995 |
| JP | 7329481 A | | 12/1995 |
| JP | 8025876 A | | 1/1996 |
| JP | 11076173 A | | 3/1999 |
| JP | 2005211649 A | | 8/2005 |
| JP | 2007003020 A | | 1/2007 |
| MX | 230716 | | 9/2005 |
| MX | 254252 | | 2/2008 |
| NZ | 513043 | | 3/2003 |
| NZ | 513044 | | 7/2003 |
| WO | 1995028181 A1 | | 10/1995 |
| WO | 1999026668 A1 | | 6/1999 |
| WO | 1999038540 A1 | | 8/1999 |
| WO | 2000006209 A2 | | 2/2000 |
| WO | 2000041733 A1 | | 7/2000 |
| WO | 2000041734 A1 | | 7/2000 |
| WO | 2001051098 A1 | | 7/2001 |
| WO | 2001070280 A1 | | 9/2001 |
| WO | 2008096123 A1 | | 8/2008 |
| WO | 2009123813 A1 | | 10/2009 |
| WO | 2013081672 A1 | | 6/2013 |
| WO | 2015013312 A1 | | 1/2015 |
| WO | 2015051024 A1 | | 4/2015 |
| WO | 2018170160 A1 | | 9/2018 |

OTHER PUBLICATIONS

Endura-Veyor Inc. (2005) "Stainless Steel Conveyors" retrieved from: https://www.endura-veyor.com/wp-content/uploads/2019/07/evi_stainless_steel_conveyors.pdf.

"PL 1300 UV Home, Autos, Marine, Motor Homes, RV's & Travel;" http://www.3rdplanetsamples.com/pl_1300_uv.htm printed Apr. 18, 2006. Cannot Find Reference.

Desktop Conveyor Belt UV LED Curing Machine; http://www.height-led.com/en/uvledbelt/show/79.html (Year: 2017). Cannot Find Reference.

International Search Report; International Application No. PCT/US2009/035885 (PCT Publication No. WO2009123813); dated May 12, 2009.

International Search Report; International Application No. PCT/US2014/047669 (PCT Publication No. WO2015013312); dated Nov. 12, 2014.

International Search Report; International Application No. PCT/US2014/058674 (PCT Publication No. WO2015051024); dated Dec. 31, 2014.

International Search Report; International Application No. PCT/US2000/000547 (PCT Publication No. WO2000041734); dated May 24, 2000.

International Search Report; International Application No. PCT/US2000/000448 (PCT Publication No. WO2000041733); dated May 24, 2000.

International Search Report; International Application No. PCT/US2020/044283 (PCT Publication No. WO2021022053); dated Oct. 26, 2020.

International Search Report; International Application No. PCT/US2018/022482 (PCT Publication No. WO2018170160); dated May 7, 2018.

International Search Report; International Application No. PCT/US1995/004650 (PCT Publication No. WO1995028181); dated Jun. 19, 1995.

International Search Report; International Application No. PCT/US1998/025053 (PCT Publication No. WO1999026668); dated Feb. 22, 1999.

International Search Report; International Application No. PCT/US1999/001597 (PCT Publication No. WO1999038540); dated Jun. 10, 1999.

International Search Report; International Application No. PCT/US2001/001169 (PCT Publication No. WO2001051098); dated Jun. 12, 2001.

International Search Report; International Application No. PCT/US2001/008665 (PCT Publication No. WO2001070280); dated Aug. 16, 2001.

International Search Report; International Application No. PCT/GB2008/000399 (PCT Publication No. WO2008096123); dated May 15, 2008.

International Search Report; International Application No. PCT/US2012/044056 (PCT Publication No. WO2013081672); dated Oct. 1, 2012.

* cited by examiner

APPARATUS AND METHOD FOR DISINFECTING SUBSTANCES AS THEY PASS THROUGH A PIPE

CROSS-REFERENCE TO RELATED APPLICATIONS

This application claims priority to U.S. Provisional Application Ser. No. 63/208,318, filed on Jun. 8, 2021, which is incorporated herein by reference.

TECHNICAL FIELD

The present disclosure relates to a disinfecting apparatus. More particularly, the present disclosure relates to a device to disinfect items such as powder or liquid as it passes through a pipe.

BACKGROUND

Infectious diseases commonly spread through the direct transfer of bacteria, viruses, or other microbes on surfaces or in water or other liquids. Various methods are employed for disinfecting items, with the most common method involving the use of chemical disinfectants. While chemical disinfectants work well in some industries, they may not be ideal in others, such as the food and drink industry. Additionally, disinfecting foods or ingredients for foods, such as flour, sugar, or powders, can be extremely difficult and often require significant modifications to a production line, which is costly.

Accordingly, there is a need for a disinfectant apparatus that can disinfect powders, liquids, and other substances without chemical treatments and that is easy to adapt to current manufacturing facilities. The present disclosure seeks to solve these and other problems.

SUMMARY OF EXAMPLE EMBODIMENTS

In some embodiments, a disinfecting apparatus comprises a flow-through device (e.g., pipe, hollow shaft, duct, tube, enclosure, etc.) configured to allow disinfecting light to penetrate therein to disinfect powder, liquid, or other substances. In some embodiments, the flow-through device comprises a window and a disinfecting light coupled to the exterior of the flow-though device and positioned to shine disinfecting light through the window so as to expose the substances passing therethrough.

In some embodiments, a method of retrofitting a current flow-through device comprises cutting an aperture in the flow-through device, covering the aperture with a window (e.g., quartz, glass, plastic, etc.), coupling a housing to the flow-through device, the housing comprising a disinfecting light configured to shine disinfecting light through the window to expose the substances flowing in the flow-through device to disinfecting light.

In some embodiments, the flow-through device comprises a plurality of windows and a plurality of disinfecting lights, each coupled to the flow-through device and configured to shine through a respective window.

In some embodiments, the flow-through device may comprise inner protrusions, fins, blades, fans, crosswise airflow, varying air pressure, or other means for disrupting the flow of the substance in order to maximize exposure to the disinfecting lights.

DETAILED DESCRIPTION OF EXAMPLE EMBODIMENTS

Figure 1:
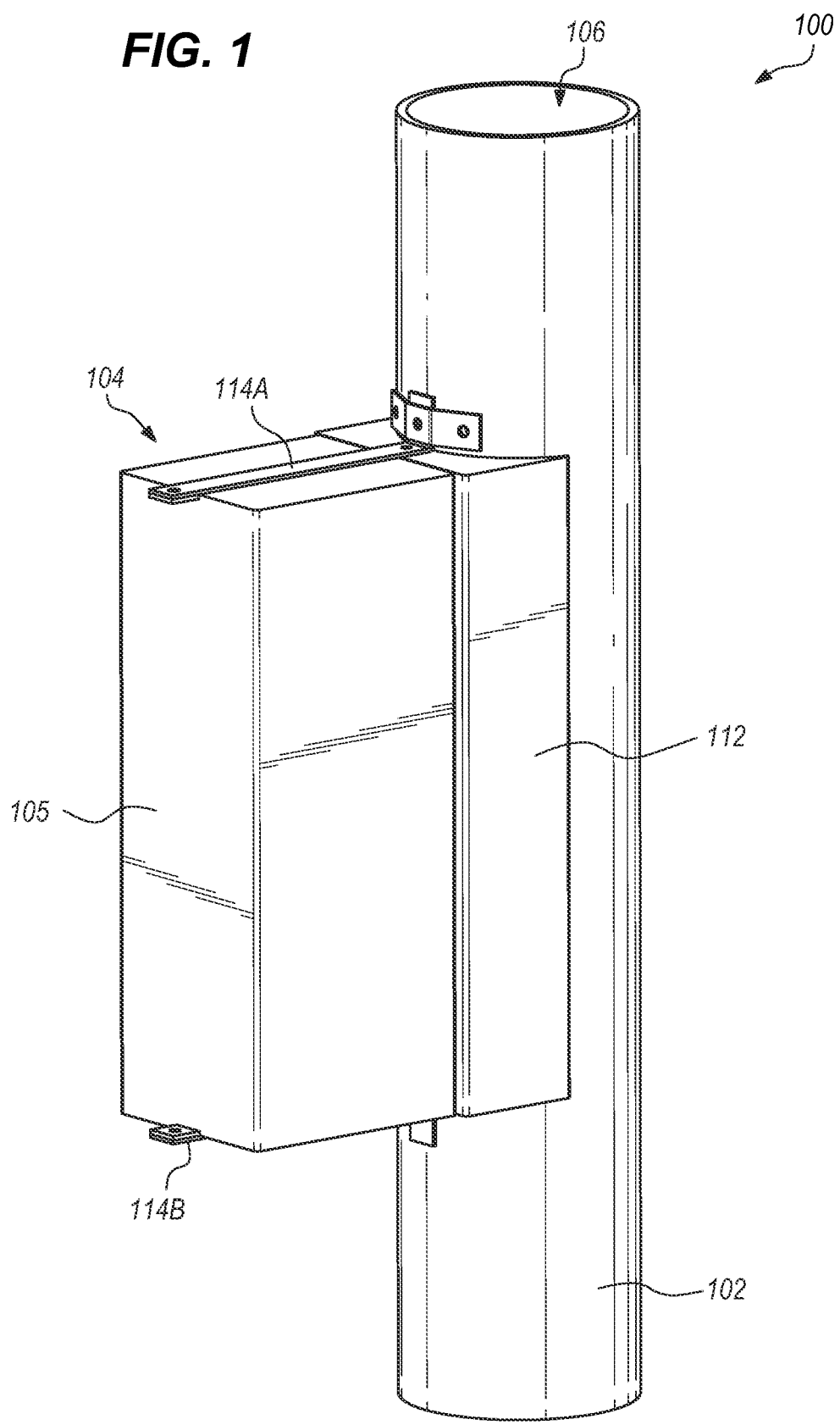
FIG. 1 illustrates a right side perspective view of a disinfecting apparatus.
Figure 2:
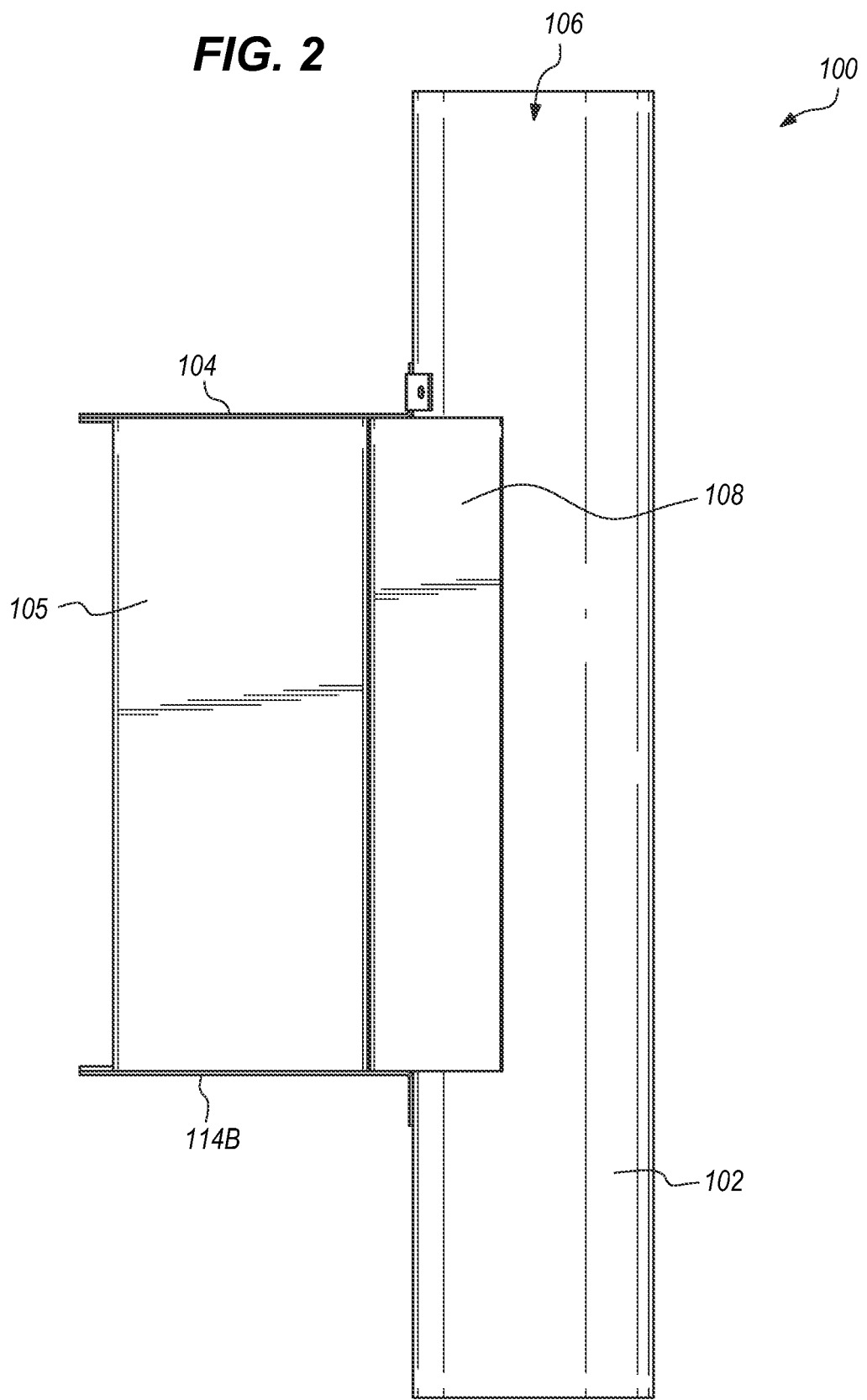
FIG. 2 illustrates a right side elevation longitudinal cross-section of a disinfecting apparatus.
Figure 3:
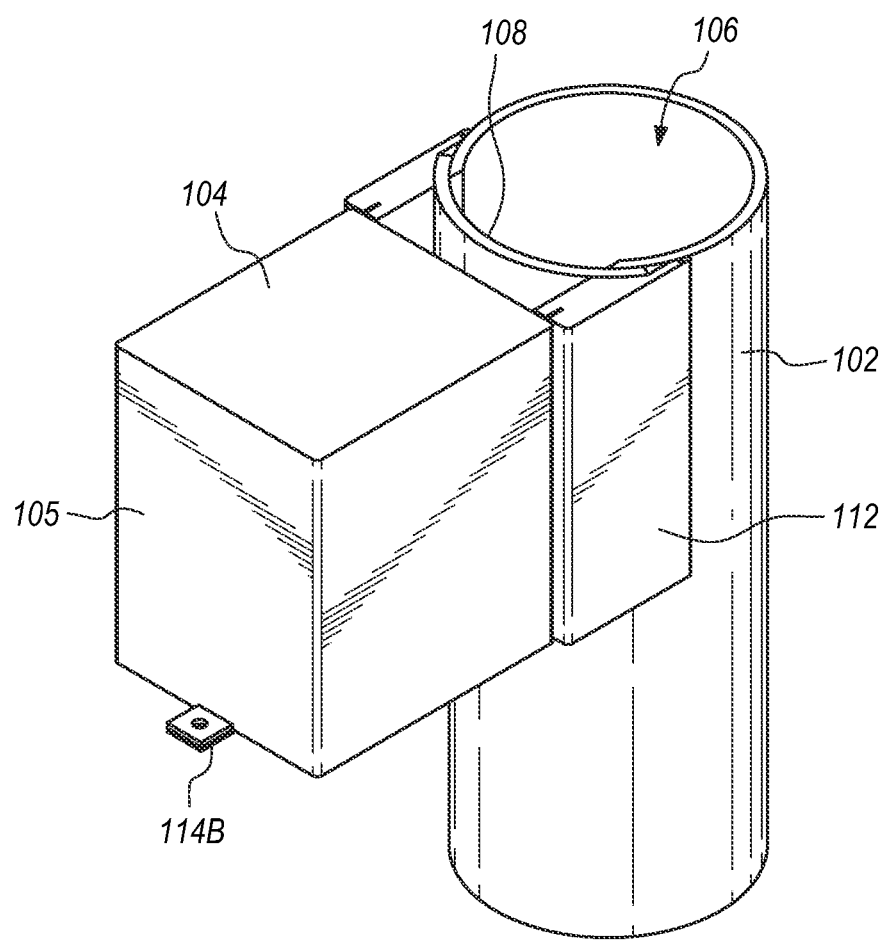
FIG. 3 illustrates a top, right side perspective horizontal cross-section of a disinfecting apparatus.
Figure 4:
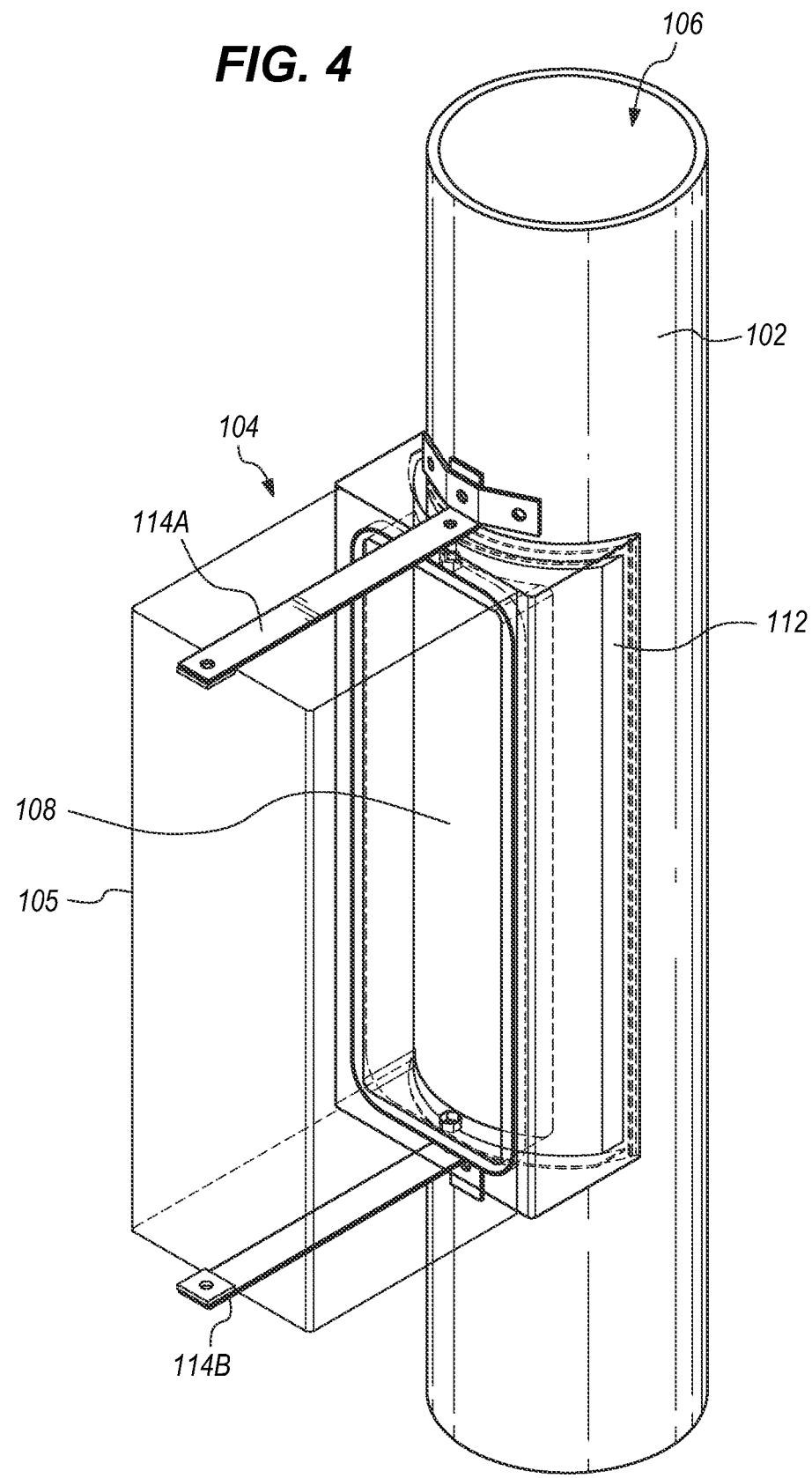
FIG. 4 illustrates a top, right side perspective view of a disinfecting apparatus.
Figure 5:
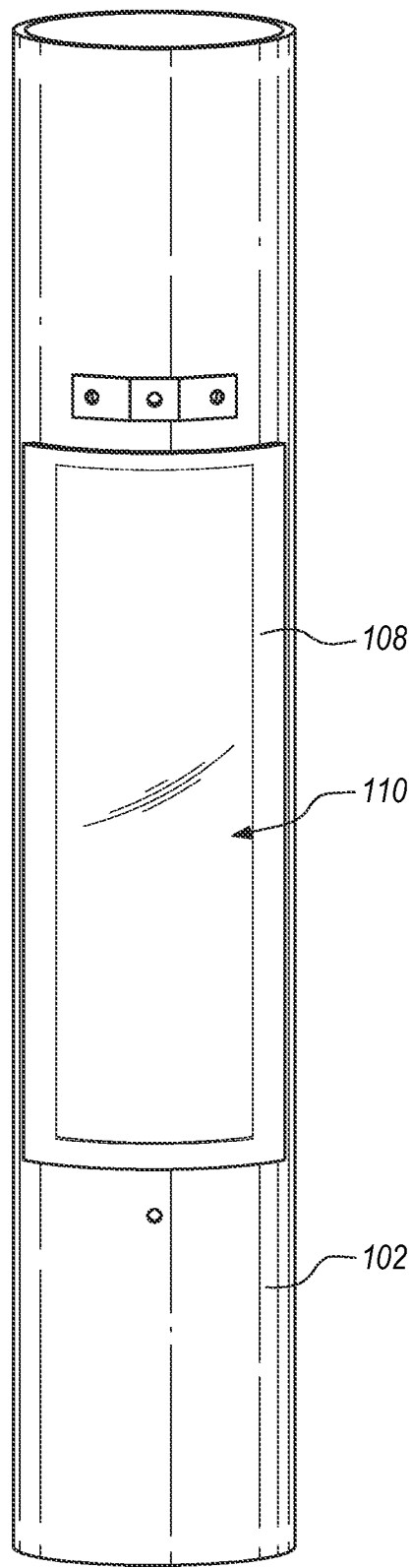
FIG. 5 illustrates a front elevation view of a pipe with a window of a disinfecting apparatus.

The following descriptions depict only example embodiments and are not to be considered limiting in scope. Any reference herein to "the invention" is not intended to restrict or limit the invention to exact features or steps of any one or more of the exemplary embodiments disclosed in the present specification. References to "one embodiment," "an embodiment," "various embodiments," and the like, may indicate that the embodiment(s) so described may include a particular feature, structure, or characteristic, but not every embodiment necessarily includes the particular feature, structure, or characteristic. Further, repeated use of the phrase "in one embodiment," or "in an embodiment," do not necessarily refer to the same embodiment, although they may.

Reference to the drawings is done throughout the disclosure using various numbers. The numbers used are for the convenience of the drafter only and the absence of numbers in an apparent sequence should not be considered limiting and does not imply that additional parts of that particular embodiment exist. Numbering patterns from one embodiment to the other need not imply that each embodiment has similar parts, although it may.

Accordingly, the particular arrangements disclosed are meant to be illustrative only and not limiting as to the scope of the invention, which is to be given the full breadth of the appended claims and any and all equivalents thereof. Although specific terms are employed herein, they are used in a generic and descriptive sense only and not for purposes of limitation. Unless otherwise expressly defined herein, such terms are intended to be given their broad, ordinary, and customary meaning not inconsistent with that applicable in the relevant industry and without restriction to any specific embodiment hereinafter described. As used herein, the article "a" is intended to include one or more items. When used herein to join a list of items, the term "or" denotes at least one of the items, but does not exclude a plurality of items of the list. For exemplary methods or processes, the sequence and/or arrangement of steps described herein are illustrative and not restrictive.

It should be understood that the steps of any such processes or methods are not limited to being carried out in any particular sequence, arrangement, or with any particular graphics or interface. Indeed, the steps of the disclosed processes or methods generally may be carried out in various sequences and arrangements while still falling within the scope of the present invention.

The term "coupled" may mean that two or more elements are in direct physical contact. However, "coupled" may also mean that two or more elements are not in direct contact with each other, but yet still cooperate or interact with each other.

The terms "comprising," "including," "having," and the like, as used with respect to embodiments, are synonymous, and are generally intended as "open" terms (e.g., the term "including" should be interpreted as "including, but not limited to," the term "having" should be interpreted as "having at least," the term "includes" should be interpreted as "includes, but is not limited to," etc.). While ultraviolet (UV) light is used as an example throughout, it will be appreciated that any light, or electromagnetic wavelength of light, capable of destroying or inhibiting the growth of microorganisms is contemplated herein as a "disinfecting light."

As previously discussed, there is a need for a disinfectant apparatus that can disinfect substances without chemical treatments and that is easy to adapt to current manufacturing facilities. The disinfecting apparatus disclosed herein solves these and other problems.

In some embodiments, as shown in FIGS. 1-7, a disinfecting apparatus 100 comprises a flow-through device (e.g., pipe) 102 configured to allow light to penetrate therein to disinfect powder, liquid, or other substances flowing through the pipe 102. For example, a disinfecting light 104 may be coupled to the exterior of the pipe 102 with the light configured to shine within the interior 106 of the pipe 102. This allows a user to readily access bulbs or other components of the disinfecting light 104.

In some embodiments, as best seen in FIGS. 2-7, the pipe 102 comprises a window 108 with the disinfecting light 104 coupled to the exterior of the flow-though device 102 and positioned to shine disinfecting light (e.g., UV light) through the window 108 so as to expose the substances (e.g., powders, liquids, etc.) passing therethrough to the UV light, thereby disinfecting the substances. In other words, the pipe 102 comprises a sidewall aperture 110 sized so as to allow the passage of UV light therethrough, a window 108 (which may be made from quartz, glass, plastic, or any other suitable transparent material), a light bracket 112 that is complementary in shape to the pipe 102 (e.g., arcuate/half-pipe) and is securable to the pipe 102. In some embodiments, the light bracket 112 may be directly fastened to the pipe 102 via screws and/or adhesives. In some embodiments, a plurality of securing straps 114A-B may be secured to the pipe 102, with the light bracket 112 securable to the securing straps 114A-B via screws, bolts, etc. Because the disinfecting light 104 is external to the pipe 102, it is readily accessible for maintenance. For example, if the disinfecting light 104 needs a bulb to be replaced, a user may easily remove the disinfecting light 104 (which may comprise a housing 105 and bulbs or other light sources therein), such as by removing screws or bolts, and replace it with a new disinfecting light 104 or may replace the internal components (e.g., bulbs) therein. Having a removably attachable disinfecting light 104 coupled to pipe 102 is a major improvement over the prior art.

Figure 6:
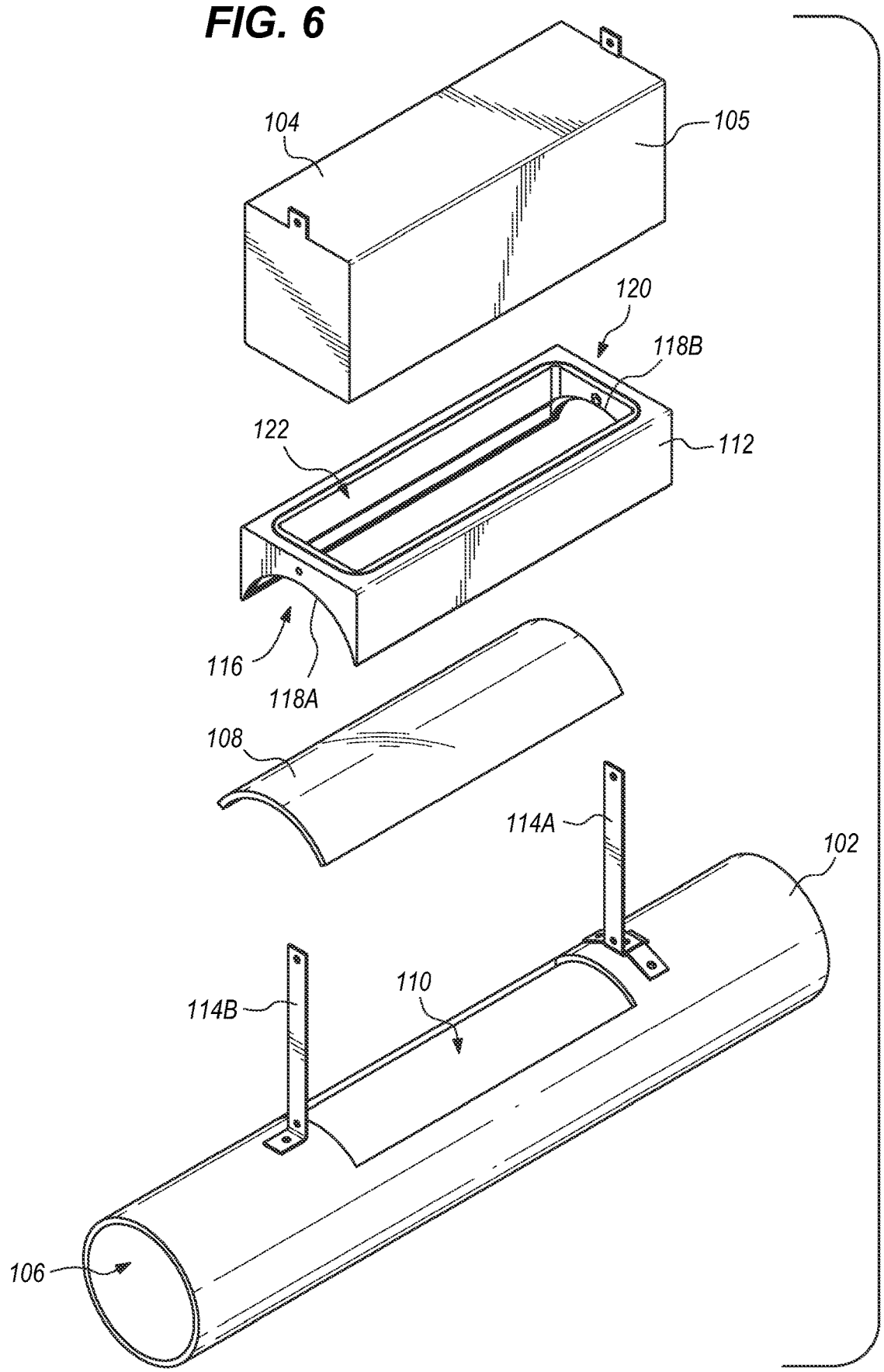
FIG. 6 illustrates an exploded view of the disinfecting apparatus.
Figure 7:
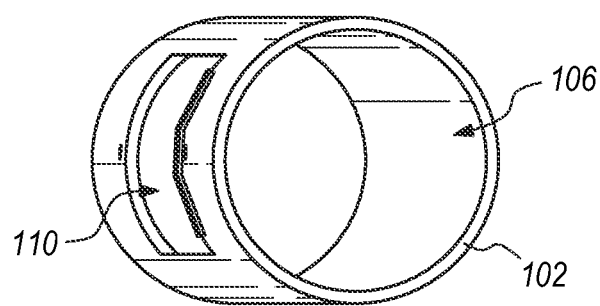
FIG. 7 illustrates a top perspective view of a pipe with a sidewall aperture of a disinfecting apparatus.

In some embodiments, as best seen in FIG. 6, the light bracket 112 comprises a first side 116 for coupling to the pipe 102. In other words, first side 116 is complementary in shape (e.g., arcuate ends 118A-B) for mating with the pipe 102. The light bracket 112 is of a sufficient size so as to encompass the sidewall aperture 110 and window 108, fully concealing the sidewall aperture 110 and window 108 within the light bracket 112. The window 108 may be coupled so as to cover the sidewall aperture 110 from the inside 106 or external surface. The window 108 may be sealed to the pipe 102 using adhesives or other materials so as to create a water-tight covering over the sidewall aperture 110. Accordingly, as substances flow through the pipe 102, nothing leaks out of the sidewall aperture 110 due to the window 108 sealed thereon. With the window 108 sealed to the pipe 102 so as to cover the sidewall aperture 110, the light bracket 112 may then be coupled to the pipe 102, such as by using adhesives, screws, etc. A second side 120 of the light bracket 112 is configured to couple with the housing 105 of the disinfecting light 104. The light bracket 112 comprises a light aperture 122, allowing light from the disinfecting light 104 to pass therethrough to the window 108 and sidewall aperture 110, where the light can disinfect substances flowing therethrough. The light housing 105 may seal to the light bracket 112 using securing straps 114A-B, and may include a sealant (e.g., rubber, silicone, etc.) therebetween in order to ensure the light does not escape.

In some embodiments, a method of retrofitting a current flow-through device (e.g., pipe) 102 comprises cutting a sidewall aperture 110 in the pipe 102, covering the sidewall aperture 110 with a window 108 that is transparent (e.g., quartz, glass, plastic, etc.), and coupling disinfecting light 104 configured to shine disinfecting light through the window 108 of to expose the substances flowing within the pipe 102 to disinfecting light. In some embodiments, the disinfecting light 104 may be coupled to the pipe 102 directly (e.g., the housing 105 may be curved complementary to the pipe 102 and secured using adhesives, screws, bolts, securing straps 114A-B, etc. In some embodiments, the disinfecting light 104 may be coupled to the pipe 102 via a light bracket 112. In other word, the light bracket 112 is interposed between the pipe 102 and the disinfecting light 104.

In some embodiments, retrofitting a pipe 102 comprises cutting and removing a length of the pipe 102, inserting a disinfecting apparatus 100 between the original remaining portions of the pipe 102, and coupling it at both ends using a coupler.

In some embodiments, the pipe 102 comprises a plurality of windows 108 and a plurality of disinfecting lights 104, each disinfecting light 104 coupled to the pipe 102 and configured to shine through a respective window 108. This may be helpful to ensure that substances flowing in the pipe 102 are adequately exposed to UV light or other disinfecting light.

Figure 8:
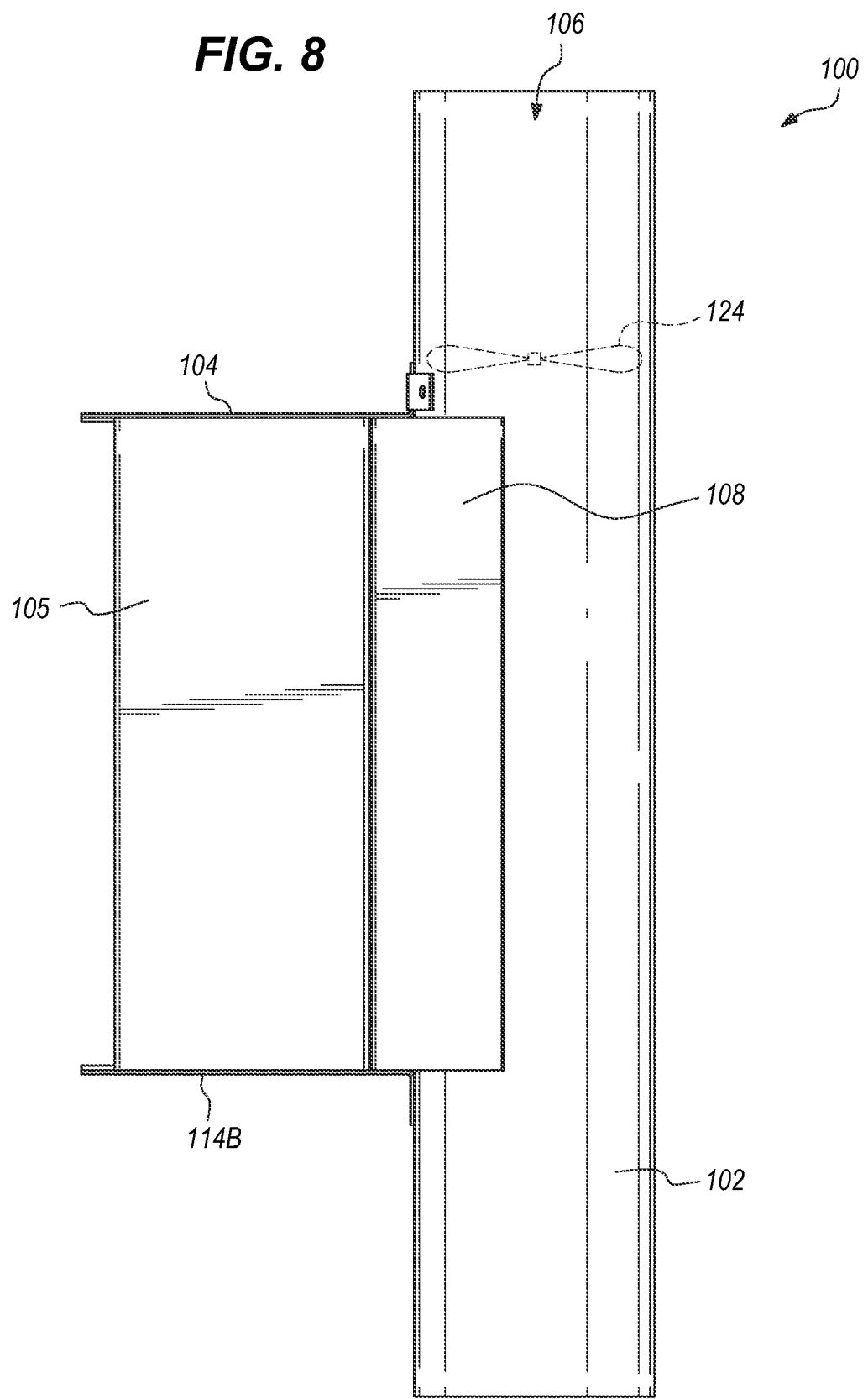
FIG. 8 illustrates a right side elevation longitudinal cross-section of a disinfecting apparatus.

Referring to FIG. 8, in some embodiments, the flow-through device (e.g., pipe 102) may comprise inner protrusions, fins, blades, fans 124, crosswise airflow, varying air pressure, or other means for disrupting the flow of the substance in order to maximize exposure to the disinfecting lights. In other words, a mass of particles (e.g., powder) may not be sufficiently exposed to the disinfecting light 104 when flowing. To ensure that all particles are exposed to the disinfecting light 104, it may be beneficial to disrupt the flow of powder. This may be accomplished in numerous ways, as mentioned above. For example, a fan 124 may disrupt the flow so that the particles separate. By disrupting the flow, each particle is more likely to be exposed to disinfecting light 104.

As a result, it will be appreciated from the foregoing that the disinfecting apparatus herein solves problems in the art, and particularly allows a user to disinfect substances/items flowing through a pipe while allowing ease of access to the disinfecting light from the outside of the pipe.

Further, although generally referred to herein as a "disinfecting apparatus," it is understood that a disinfecting apparatus of the present disclosure may disinfect, sterilize, sanitize, or otherwise treat and clean substances to achieve a lessened state or condition of contamination.

It will also be appreciated that systems and methods according to certain embodiments of the present disclosure may include, incorporate, or otherwise comprise properties or features (e.g., components, members, elements, parts, and/or portions) described in other embodiments. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment unless so stated. Rather, it will be appreciated that other embodiments can also include said features, members, elements, parts, and/or portions without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative systems, methods, apparatus, and the like are not described herein in particular detail in order to avoid obscuring aspects of the example embodiments. Such aspects are, however, also contemplated herein.

Exemplary embodiments are described above. No element, act, or instruction used in this description should be construed as important, necessary, critical, or essential unless explicitly described as such. Although only a few of the exemplary embodiments have been described in detail herein, those skilled in the art will readily appreciate that many modifications are possible in these exemplary embodiments without materially departing from the novel teachings and advantages herein. Accordingly, all such modifications are intended to be included within the scope of this invention.

What is claimed is:

1. A disinfecting apparatus, comprising:
    a pipe having a constant, unchanging diameter and comprising a sidewall aperture;
    a transparent window sealed over the sidewall aperture;
    a first securing strap extending perpendicularly from the pipe above a first end of the transparent window, and a second securing strap extending perpendicularly from a second end of the transparent window;
    a light bracket extending longitudinally along the pipe and coupled to the exterior of the pipe over the transparent window and in between the first and second securing straps, the light bracket comprising:
        a first side comprising a first arcuate end and a second arcuate end for coupling to the pipe,
        a second side distal to the pipe, the second side comprising a light aperture aligned with the transparent window;
    a removably attachable disinfecting light coupled to the second side of the light bracket via the first securing strap on a first end of the light bracket and a second securing strap on a second end of the light bracket, the disinfecting light configured to shine through the light aperture of the bracket and through the transparent window into the pipe; and
    a fan positioned within the pipe to agitate the flow of substances as they pass through the pipe.

2. The disinfecting apparatus of claim 1, wherein the fan is configured to agitate non-liquid substances.

* * * * *